United States Patent
Tanaka et al.

(10) Patent No.: US 6,506,793 B2
(45) Date of Patent: Jan. 14, 2003

(54) CITRAL ACETAL

(75) Inventors: Sakuya Tanaka, Wakayama (JP); Shigeyoshi Tanaka, Wakayama (JP); Shunichi Akiba, Tochigi (JP); Katsutoshi Ara, Tochigi (JP); Hirohiko Ishida, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/973,017

(22) Filed: Oct. 10, 2001

(65) Prior Publication Data

US 2002/0068075 A1 Jun. 6, 2002

(30) Foreign Application Priority Data

Oct. 13, 2000 (JP) .......................................... 2000-312869

(51) Int. Cl.$^7$ ....................... A61K 31/335; A61K 31/34; A61K 31/045; A61K 6/00
(52) U.S. Cl. ....................... 514/463; 514/461; 514/449; 514/729; 514/739; 424/401
(58) Field of Search ........................... 424/401; 514/463, 514/449, 461, 729, 739

(56) References Cited

U.S. PATENT DOCUMENTS

| 5,378,468 A | 1/1995 | Suffis et al. |
| 5,626,852 A | 5/1997 | Suffis et al. |

FOREIGN PATENT DOCUMENTS

| JP | 11-513742 | 11/1999 | |
| WO | WO 97/34986 | 9/1997 | |
| WO | WO 00/04009 | * 1/2000 | .......... C07D/317/32 |

OTHER PUBLICATIONS

Kamogawa et al., Bull. Chem. Soc. Jpn. (1981), 54(5), 1577–8 (abstract, Accession No.: 1981:497641 CAPLUS).*
Kamogawa et al., Chem. Soc. Jpn. (1981), 54(5), 1577–1578 (Accession Number 1981:497641 CAPLUS).

* cited by examiner

*Primary Examiner*—Russell Travers
*Assistant Examiner*—S. Jiang
(74) *Attorney, Agent, or Firm*—Oblon, Spivak, McClelland, Maier & Neustadt, P.C.

(57) ABSTRACT

The present invention provides a citral acetal capable of sustaining a lemon aroma unique to citral and a perfume composition comprising the citral acetal, as well as an LDH inhibitor and a deodorant, cosmetics and a skin agent for external application, comprising the LDH inhibitor. The citral acetal of the present invention is represented by formula (1):

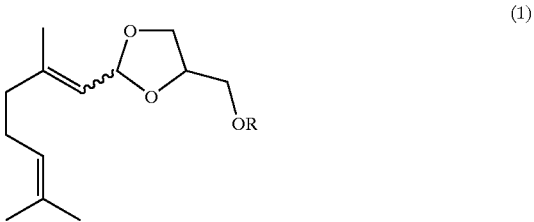

(1)

wherein the wavy line represents a cis and/or trans form, and R represents a $C_1$ to $C_9$ linear or branched alkyl group.

15 Claims, 7 Drawing Sheets

CITRAL ACETAL

FIELD OF THE INVENTION

The present invention relates to a citral acetal from which citral is sustainedly released and to a perfume composition comprising the citral acetal useful as an ingredient incorporated into toiletries and cosmetics. The present invention also relates to an inhibitor of leucine dehydrogenase (referred to hereinafter as LDH) involved in a metabolic pathway of isovaleric acid as a component in body smell and to a deodorant, cosmetics and a skin agent for external application, comprising the LDH inhibitor.

PRIOR ART

Citral is a perfume having a strong lemon-like aroma contained in natural lemon oil, lemon-grass oil etc., but it is highly volatile and instable to air, sunrays and alkalis, thus hardly sustaining its aroma. To solve this problem, citral dimethyl acetal and citral diethyl acetal have been used, but these compounds possess not lemon aromas but neroli-like citrus green aromas, and do thus not possess the lemon-like aroma of citral. Further, JP-A 11-513742 (WO97/34986) discloses a method of sustainedly releasing citral by converting it into acetals having molecular weights of 350 or more, for example into di-geranyl citral acetal and then hydrolyzing these acetals to release citral sustainedly, but these are high-molecular compounds to which purification techniques such distillation cannot be applied, and perfumes formed therefrom are geraniol and citral, thus making it difficult to reproduce the lemon-like aroma unique to citral. Against these problems, U.S. Pat. No. 5378468 describes that citral is sustainedly released by hydrolysis of citral propylene glycol acetal using propylene glycol having a weak aroma, but it was recognized that this acetal itself is volatile and has a green aroma, thus inhibiting the lemon aroma unique to citral.

Meanwhile, various techniques of suppressing body smell have been developed for inclinations toward cleanliness in recent years. In particular, use of antimicrobial agents and bactericides can be mentioned as the most popular method of suppressing body smell from of old. This method is a method of killing bacteria present on the skin, and can be easily completed thereby giving a feeling of significant effect. However, some bacteria inhabiting on the skin take responsibility for the barrier function of the skin, and it was also reported that the method of killing all bacteria is unfavorable for the human body in the long run, and therefore the antimicrobial agents and bactericides came to be avoided. U.S. Pat. No. 5626852 describes that citral is sustainedly released by hydrolysis of citral propylene glycol acetal using propylene glycol having a weak aroma.

SUMMARY OF INVENTION

An object of the present invention is to provide a citral acetal capable of sustaining a lemon aroma unique to citral, as well as a perfume composition comprising the same. Another object of the present invention is to provide an LDH inhibitor capable of suppressing unpleasant human body smell by enzyme inhibition not harmful to the human body, that is, by inhibiting enzymatic formation of isovaleric acid regarded as one substance causing unpleasant body smell. The invention then provides a deodorant, cosmetics and a skin agent for external application, comprising the LDH inhibitor.

Under these circumstances, the present inventors found that an acetal of citral with a specific glyceryl ether can be easily purified and can, upon hydrolysis, sustainedly release a lemon aroma unique to citral, and also that this citral acetal has an activity of inhibiting LDH derived from bacteria living on the skin, for example Bacillus bacteria, involved in a pathway of forming isovaleric acid regarded as one substance causing unpleasant human body smell, and the present invention was thereby completed.

That is, the present invention provides a citral acetal represented by formula (1) (referred to hereinafter as citral acetal (1)), a perfume composition comprising citral acetal (1), an LDH inhibitor comprising citral acetal (1), a deodorant, cosmetics and a skin agent for external application, comprising said LDH inhibitor.

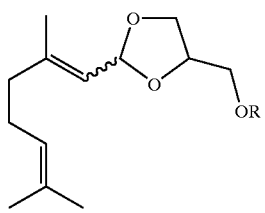

(1)

wherein the wavy line represents a cis form, trans form or a mixture thereof and R represents a $C_1$ to $C_9$, linear or branched alkyl group.

The citral acetal of the invention is a reaction product of citral and a glycerin alkyl-monoether. The alkyl may have 1 to 9 carbon atoms.

The invention further provides a leucine dehydrogenase (LDH) inhibitor composition comprising the citral acetal compound as above and a carrier. It moreover provides a leucine dehydrogenase (LDH) inhibitor composition comprising the citral acetal compound as above and a perfume, a deodorant, a cosmetic or a skin agent for external application.

The invention then provides a method of inhibiting leucine dehydrogenase (LDH) on the human skin, which comprising applying an effective amount of the citral acetal compound as above onto the human skin.

The invention provides a method of sustainedly releasing an aroma of citral, which comprises applying an effective amount of the above defined citral acetal compound to a place (locus or spot) where the aroma of citral is desired.

DETAILED DESCRIPTION OF INVENTION

The citral acetal (1) can be produced by reacting citral with a glyceryl ether represented by formula (2) (referred to hereinafter as glyceryl ether (2)) according to a conventional method, for example a method described in "Jikken Kagaku Koza" (Course on Experimental Chemistry), 4th ed., vol. 20, p. 245.

$$CH_2(OH)CH(OH)CH_2OR \quad (2)$$

wherein R has the same meaning as defined above.

The glyceryl ether (2) is the one containing 4 to 12 carbon atoms, and examples thereof include methyl glyceryl ether, ethyl glyceryl ether, n-propyl glyceryl ether, isopropyl glyceryl ether, n-butyl glyceryl ether, n-pentyl glyceryl ether, isopentyl glyceryl ether, n-hexyl glyceryl ether, 2-ethyl hexyl glyceryl ether, n-heptyl glyceryl ether, n-octyl glyceryl ether, n-nonyl glyceryl ether etc. The glyceryl ether (2) is used preferably in an amount of 0.5- to 5.0 times as many moles as citral, more preferably 1.0- to 2.0 times.

As the catalyst for reaction of citral with glyceryl ether (2), use can be made of an inorganic acid such as hydrochloric acid, an organic acid such as p-toluenesulfonic acid, citric acid or tartaric acid, and a catalyst carrying sulfonic acid, such as Amberlite 15, among which a mild acid such as citric acid or tartaric acid is preferably used. The catalyst is used preferably in an amount of 0.0001- to 0.5 time as many moles as citral, more preferably 0.001- to 0.1 time, the most preferably 0.002-to0.05 time. This reaction is an equilibrium reaction so that for shifting the equilibrium to the side of acetal, the reaction may be carried out either while removing water through azeotropic distillation with a solvent such as benzene, toluene, cyclohexane, hexane or petroleum ether, or in the presence of a dehydrating agent such as magnesium sulfate. When the dehydrating agent is used, it may be used in an amount of 1- to 2 times as many moles as the formed water. The solvent is used preferably in an amount of 0.5 to 20 times as much weight as citral, more preferably 1 to 10 times.

The reaction temperature is preferably 30 to 150° C., more preferably 50 to 100° C. The reaction time is varied depending on reaction conditions, but usually the reaction is finished in 6 to 60 hours. After the reaction is finished, the desired citral acetal is obtained from the reaction solution by techniques such as neutralization, filtration, distillation and extraction. If necessary, the product is further purified by conventional methods such as silica gel chromatography, distillation etc.

The citral acetal (1) can maintain a lemon aroma unique to citral for a prolonged period of time. Further, the citral acetal (1) has an activity of inhibiting LDH derived from bacteria living on the skin, such as Bacillus bacteria, involved in a pathway of forming isovaleric acid regarded as one substance causing unpleasant human body smell, and thus the citral acetal (1) is useful as an LDH inhibitor.

The perfume composition of the present invention comprising citral acetal (1) may comprise at least one kind of citral acetal (1), or known perfume ingredients (e.g., perfume ingredients described in "Gosei Koryo, Kagaku to Shohin Chishiki" (Synthetic Perfumes, Chemistry and Commodity Knowledge), first ed., authored by Genichi Indo, Mar. 6, 1996, published by Kagaku Kogyo Nipposha) blended with at least one kind of citral acetal (1). Although the content of citral acetal (1) in the perfume composition of the present invention is varied depending on the type of composition and the type of intended blended perfume, the content of citral acetal (1) in the composition is preferably 0.01 to 90% by weight, particularly preferably 0.1 to 50% by weight. If necessary, other additives for example an antioxidant selected from phenols such as 2,6-di-tert-butyl hydroxy toluene (BHT) and 2(3)-tert-butyl-4-hydroxy anisole (BHA), hydroquinone or analogues thereof such as tert-butyl hydroquinone (TBHQ), anti-oxidants such as tocopherols and a pH regulator selected from organic acids such as fatty acid, citric acid, tartaric acid and hexahydrophthalic acid and/or salts thereof, inorganic acids such as phosphoric acid and/or inorganic salts such as phosphate can be compounded into the perfume composition of the present invention insofar as the effect of the present invention is deteriorated.

The citral acetal (1) of the present invention can not only maintain a lemon aroma unique to citral for a prolonged period of time but also has the activity of inhibiting LDH and inhibit formation of isovaleric acid regarded as one substance causing human unpleasant smell. Accordingly the citral acetal (1) can, singly or in combination with other ingredients, be used as a component in soap, shampoos, rinses, detergents, cosmetics, deodorants, aromatics, bathing agents, coloring agents, hair colors, antimicrobial agents, anti-fungal agents, dehumidifying agents, bedclothes, towels, clothing, tissue, toilet sand for pets, chewing gum, facial packs, clay compositions for handcrafts, absorbents, cosmetics for massage, coatings, agrochemicals, medicines and ink.

A deodorant containing the LDH inhibitor of the present invention comprising the citral acetal (1) can sustainedly control unpleasant body smell without killing skin inhabitant bacteria involved in maintaining the barrier function of the skin. That is, isovaleric acid regarded as one substance causing unpleasant human body smell is formed from leucine contained in sweat via metabolism by bacteria inhabiting on the skin, such as Bacillus bacteria, and the citral acetal (1) can inhibit bacterial formation of isovaleric acid from leucine, thus certainly controlling unpleasant body smell.

The content of the citral acetal (1) in the deodorant of the present invention is preferably 0.1 to 20% by weight, more preferably 0.5 to 10% by weight.

Further, the LDH inhibitor of the present invention can be used as pharmaceutical preparations such as cosmetics, pharmaceutical preparations for external application (e.g. skin agents for external application) or non-medical preparations, for example in the form of cream, milky lotion, lotion, powder, spray or stick.

For use as cosmetics, medicines for external application or non-medical preparations, the content of citral acetal (1) therein is preferably 0.01 to 20% by weight, more preferably 0.1 to 10% by weight and most preferably 0.5 to 5% by weight.

The resulting cosmetics, medicines for external application or non-medical preparations can be combined arbitrarily with a wide variety of ordinarily used ingredients, for example cosmetic ingredients such as generally used oils, surfactants, alcohols, chelating agents, pH adjusting agents, preservatives, thickeners, pigments and perfumes, as well as UV absorbers, whiteners, wrinkle improvers, humectants, skin-secretion inhibitors, softeners, collagen-protecting agents, efficacious agents, antioxidants and solvents to manufacture the intended preparations.

By applying the cosmetics and skin agents for external application according to the present invention onto sites such as legs, sides, heads, genitals etc. where unpleasant smell can easily occur, occurrence of unpleasant smell can be regulated. The amount of the present cosmetics or skin agents for external application used, though varied depending on the content of citral acetal (1), is preferably 1 to 20 mg/cm$^2$ skin in the case of liquid preparation or 1 to 50 mg/cm$^2$ skin in the case of solid preparation.

EXAMPLES

In the Examples, "parts" and "%" refer to parts by weight and % by weight respectively unless otherwise specified.

Example 1 (Citral pentyl glyceryl ether acetal)

45.6 g (0.3mol) citral, 53.5 g (0.33 mol) pentyl glyceryl ether (=a mixture of n-pentyl glyceryl ether/iso-pentyl glyceryl ether in a ratio of 65/35), 300 mL toluene and 5.8 g citric acid were introduced into a 500-mL four-necked flask, and stirred under heating at 110° C. while water was azeotropically distilled away. After 14 hours when formed water was completely distilled away, the reaction solution was neutralized with aqueous saturated bicarbonate, dried over magnesium sulfate anhydride and separated by filtration, and the solvent was distilled away. The resulting oily residue was distilled under reduced pressure, and after the remaining citral was distilled away, the reaction product was purified by silica gel chromatography with a mixed solvent of 15% ethyl acetate/hexane, whereby 85.6 g (0.29 mol) citral pentyl glyceryl ether acetal (referred to hereinafter as the present compound 1) was obtained (yield 96%)

Figure 1:
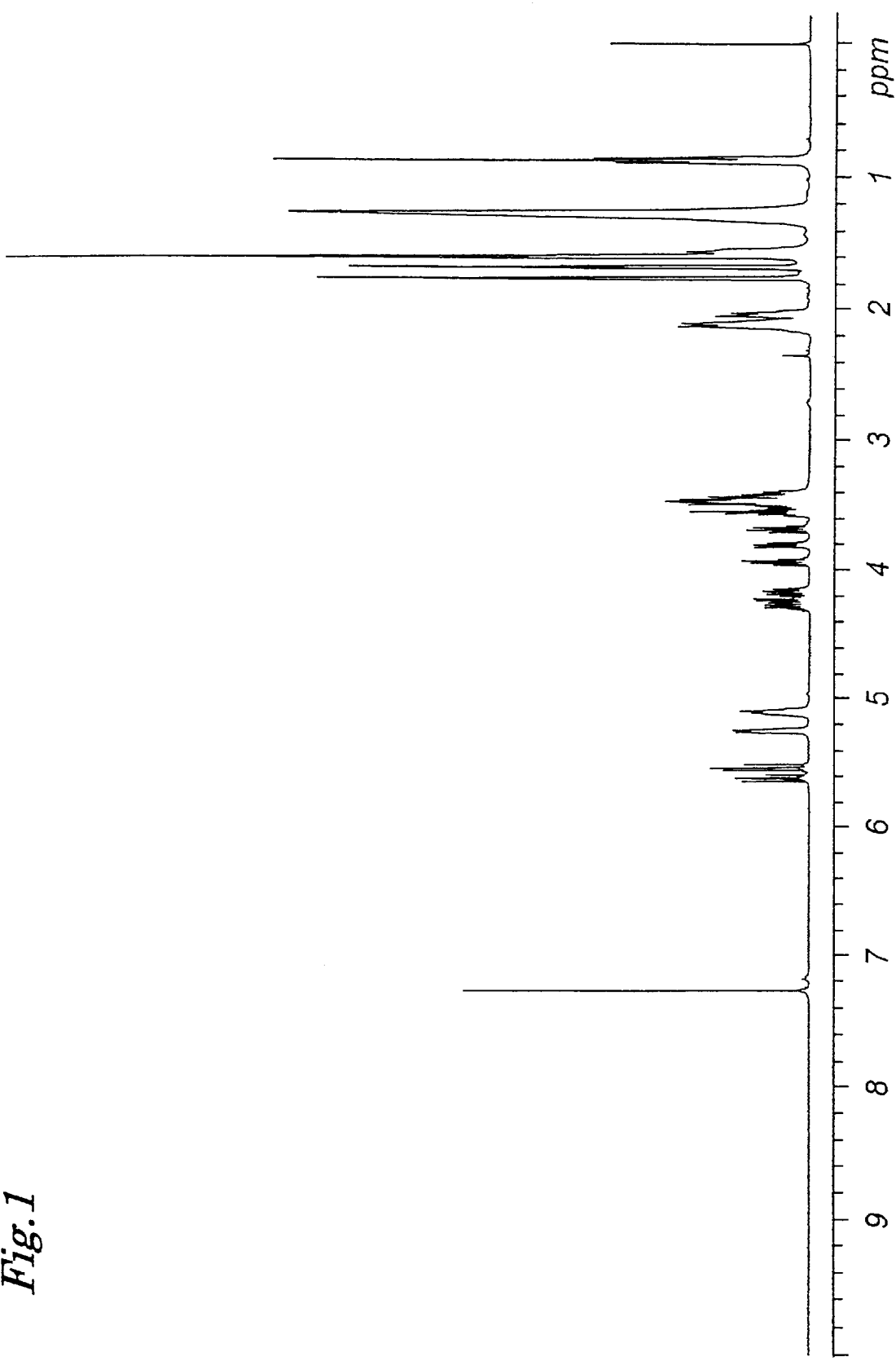
FIG. 1 is a $^1$H-NMR spectrum of the present compound 1 (400 MHz, CDCl$_3$)
Figure 2:
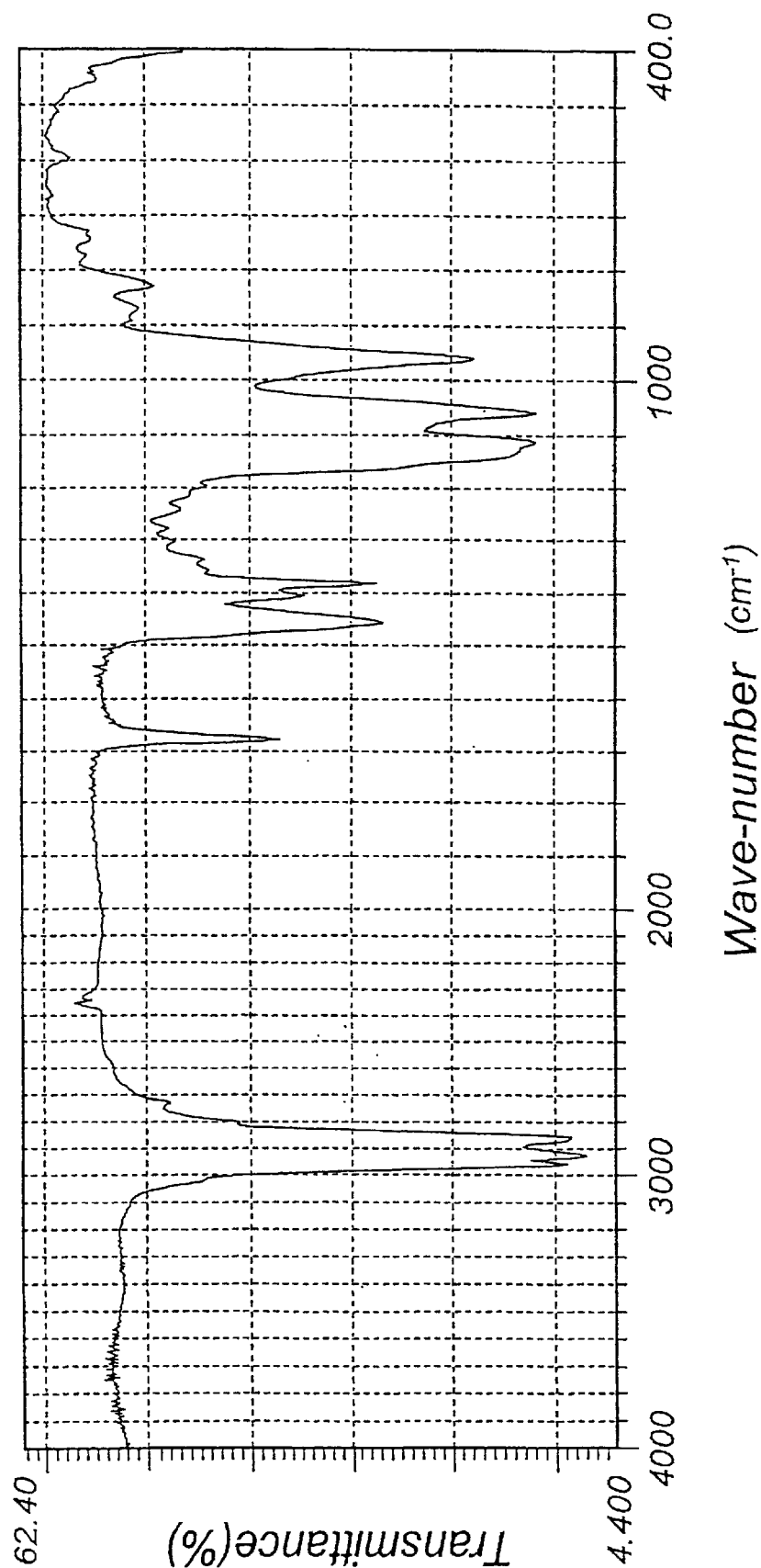
FIG. 2 is an infrared absorption spectrum of the present compound 1.

A $^1$H-NMR spectrum of the present compound 1 (400 MHz, $CDC_3$) is shown in FIG. 1 and an infrared absorption spectrum thereof is shown in FIG. 2.

Example 2 (Citral n-octyl glyceryl ether acetal)

85.0 g (0.25 mol) citral n-octyl glyceryl ether acetal (referred to hereinafter as the present compound 2) was obtained (yield 84%) by the same reaction as in Example 1 except that 67.3 g (0.33 mol) n-octyl glyceryl ether was used in place of pentyl glyceryl ether.

Figure 3:
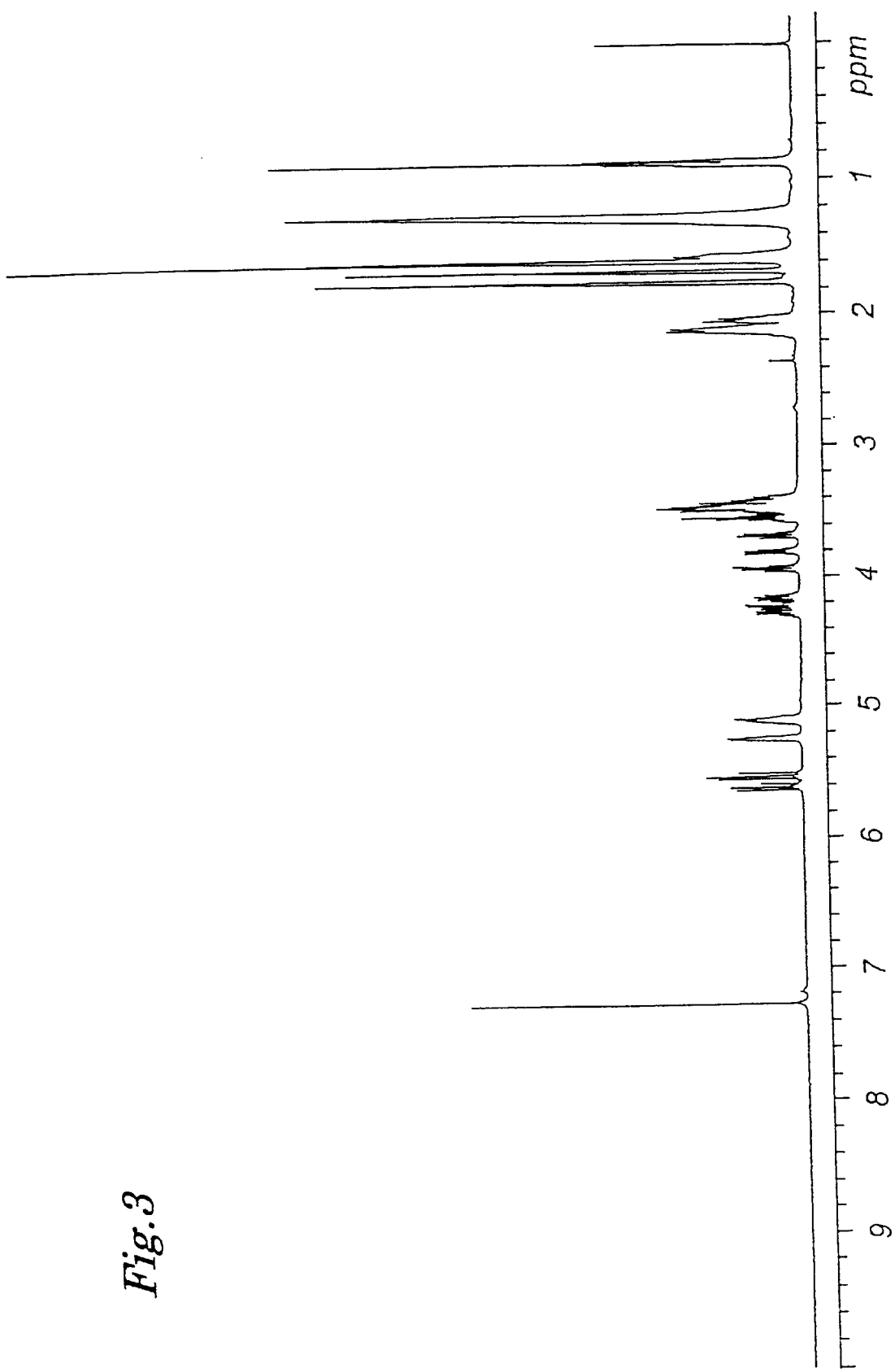
FIG. 3 is a $^1$H-NMR spectrum of the present compound 2 (400 MHz, CDCl$_3$)
Figure 4:
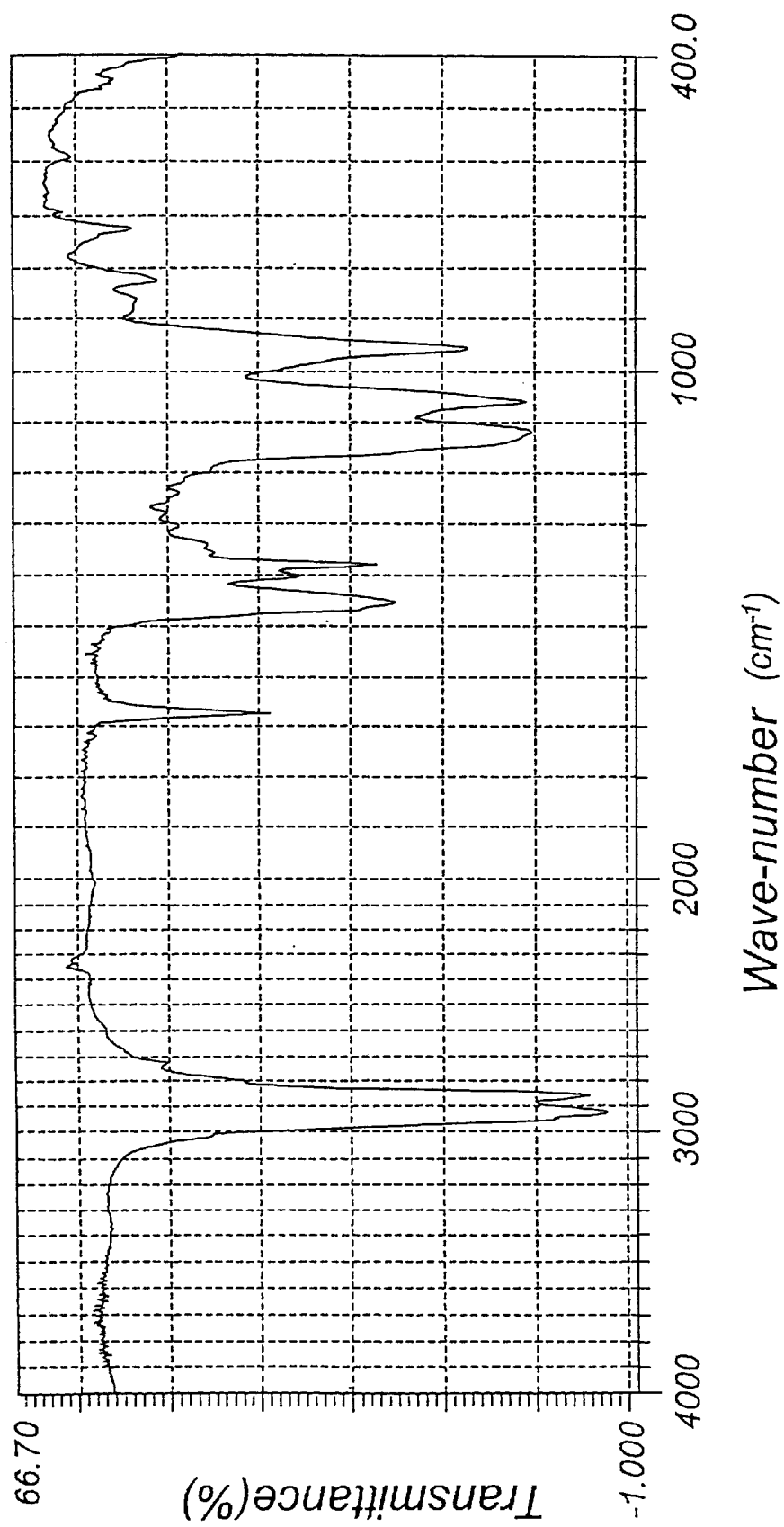
FIG. 4 is an infrared absorption spectrum of the present compound 2.

A $^1$H-NMR spectrum of the present compound 2 (400 MHz, $CDCl_3$) is shown in FIG. 3 and an infrared absorption spectrum thereof is shown in FIG. 4.

Example 3 (Citral 2-ethyl hexyl glyceryl ether acetal)

15.2 g (0.1 mol) citral, 20.4 g (0.1 mol) 2-ethyl hexyl glyceryl ether, 200 mL hexane and 2 mg p-toluenesulfonic acid were introduced into a four-necked flask, and stirred under heating at 90° C. while water was azeotropically distilled away. After 27 hours when formed water was completely distilled away, the reaction solution was neutralized with aqueous saturated bicarbonate, dried over potassium carbonate anhydride and separated by filtration, and the solvent was distilled away. The resulting oily residue was distilled under reduced pressure, and after the remaining citral was distilled away, the reaction product was purified by silica gel chromatography with a mixed solvent of 10% ethyl acetate/hexane, whereby 24 g (0.07 mol) citral 2-ethyl hexyl glyceryl ether acetal (referred to hereinafter as the present compound 3) was obtained (yield 70%).

Figure 5:
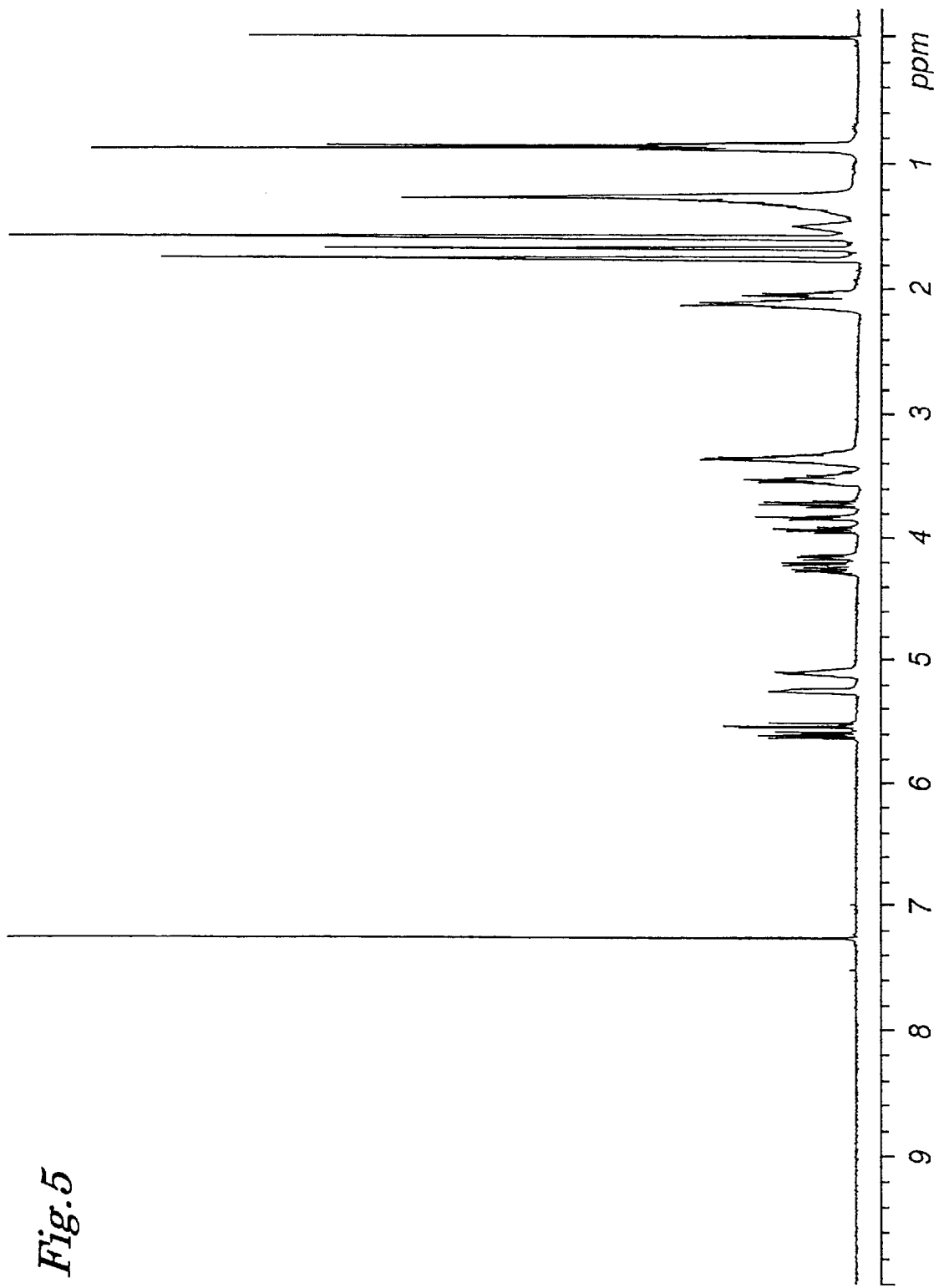
FIG. 5 is a $^1$H-NMR spectrum of the present compound 3 (400 MHz, CDCl$_3$)
Figure 6:
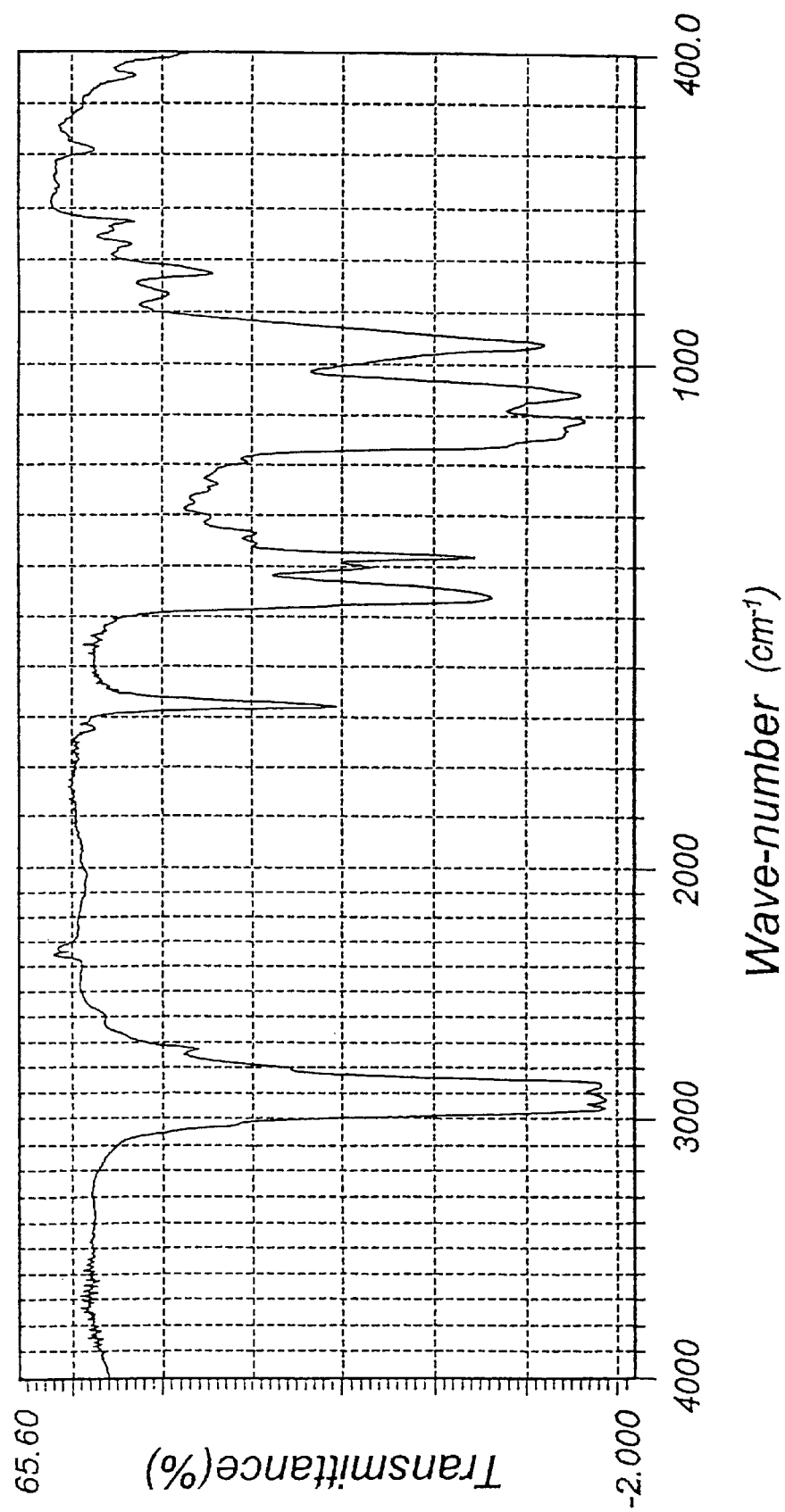
FIG. 6 is an infrared absorption spectrum of the present compound 3.

A $^1$H-NMR spectrum of the present compound 3 (400 MHz, $CDCl_3$) is shown in FIG. 5 and an infrared absorption spectrum thereof is shown in FIG. 6.

Test Example 1 (Measurement of Sustained Release)

Each of the present compounds 1 to 3 obtained in Examples 1 to 3, and each of commercial citral dimethyl acetal (CITRAL DMA produced by IFF), citral diethyl acetal (CITRAL DEA produced by Hasegawa Koryo Co., Ltd.), citral propylene glycol acetal (CITRAL PGA produced by Inoue Koryo Co., Ltd.) and citral as comparative compounds was impregnated in an amount of 0.5 g (in terms of the amount of citral therein) into 5 cm × 5 cm filter paper (1.5 mm in thickness) and left in a room not exposed to direct sunrays, and the extent of aroma in a position apart by 10 cm from each sample was subjected to organoleptic evaluation with time by one skilled examiner in the following 6-level criteria. The results are shown in Table 1.

TABLE 1

| Strength of Aroma | Present Products | | | Comparative Products | | | |
| --- | --- | --- | --- | --- | --- | --- | --- |
| | Present Compound 1 | Present Compound 2 | Present Compound 3 | CITRAL DMA | CITRAL DEA | CITRAL PGA | citral |
| Just after application | 0 | 0 | 0 | 3 | 4 | 0 | 5 |
| After 2 days | 0 | 0 | 0 | 3 | 2 | 0 | 4 |
| After 1 week | 1 | 1 | 1 | 0 | 1 | 1 | 0 |
| After 2 weeks | 2 | 2 | 2 | 0 | 0 | 1 | 0 |
| After 3 weeks | 2 | 2 | 2 | 0 | 0 | 0 | 0 |
| After 4 weeks | 1 | 1 | 1 | 0 | 0 | 0 | 0 |
| Aroma | lemon-like | lemon-like | lemon-like | citrus green (neroli-like) | citrus green (neroli-like) | weak citrus green | lemon-like |

<6-level criteria>
5: Strong
4: Slightly strong
3: Moderate
2: Slightly weak
1: Weak
0: Does not smell As is evident from Table 1, all the present compounds emitted a lemon aroma unique to citral over 1 to 4 weeks.

Test Example 2 (Measurement of the Activity of Inhibiting LDH)

Figure 7:
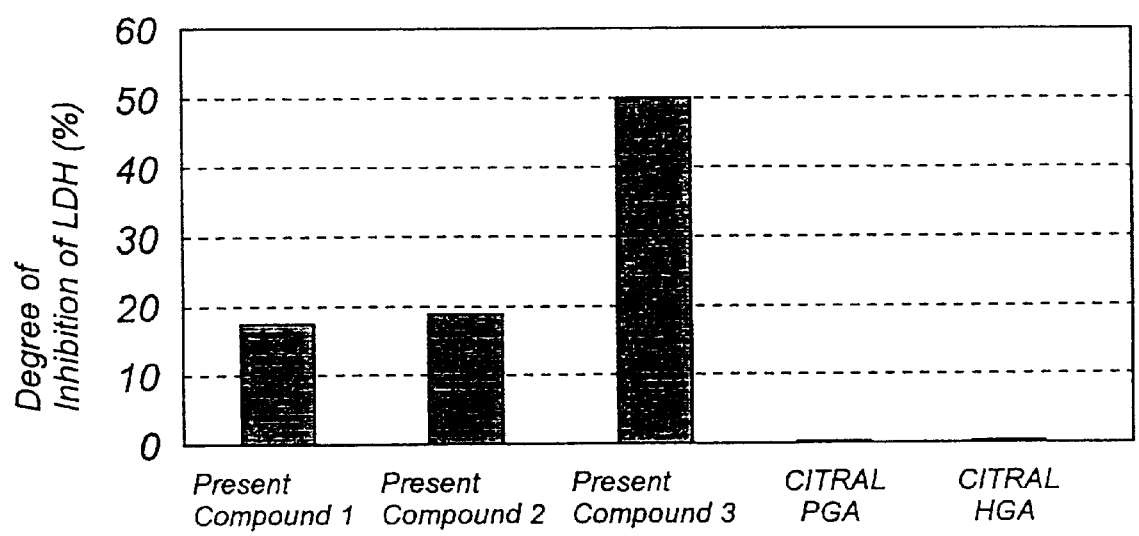
FIG. 7 is a graph showing the results of measurement of the activity of inhibiting LDH, which was conducted in Test

The present compounds 1 to 3 obtained in Examples 1 to 3, as well as commercial citral propylene glycol acetal (CITRAL PGA produced by Inoue Koryo Co., Ltd.) and citral hexylene glycol acetal (CITRAL HGA produced by Inoue Koryo Co., Ltd.) as comparative compounds, each in solution at a concentration of 0.1%, were examined for their activity of inhibiting LDH in the following manner. The results are shown in FIG. 7.

METHOD OF MEASURING THE ACTIVITY OF INHIBITING LDH

The activity of inhibiting LDH was measured in terms of the degree of inhibition of coenzyme NADH formation. Each measurement solution was 3 mL solution (30° C.) consisting of 1.5 mL of 0.25 M glycine buffer (pH 10.5), 1.0 mL of 60 mM L-leucine solution, 0.093 mL of 100 mM $AND^+$, 0.03 mL of each test sample solution and 0.337 mL water, while the control solution was 3 mL solution consisting of 1.5 mL of 0.25 M glycine buffer (pH 10.5), 1.0 mL of 60 mM L-leucine solution, 0.093 mL of 100 mM $NAD^+$ and 0.34 mL water. 10 μL LDH was added to each measurement solution and control solution respectively. After 5 minutes, the absorbance at 340 nm was measured at 30° C., then the amount of NADH formed by reduction of $NAD^+$ was determined, and the degree of inhibition of LDH was calculated using the following equation:

Degree of inhibition of LDH (%)=(A/B)×100

A: (Absorbance of each test sample after 5 minutes)–(absorbance of the blank after 5 minutes)

B: (Absorbance of the blank after 0 minute)–(absorbance of the blank after 5 minutes)

Test Example 3 (Organoleptic Evaluation)

The present compounds 1 to 3 obtained in Examples 1 to 3, as well as commercial citral propylene glycol acetal (CITRAL PGA produced by Inoue Koryo Co., Ltd.) and citral hexylene glycol acetal (CITRAL HGA produced by Inoue Koryo Co., Ltd.) as comparative compounds, were used to prepare 0.1% solutions in ethanol respectively, and 2 g solution was applied onto a bare foot. 2 g ethanol (containing no test sample) was applied onto the other bare foot (blank), then socks were put on the feet respectively, and the extent of smell (isovaleric acid) of the socks after 8 hours was subjected to organoleptic evaluation by one skilled examiner in the following 6-level criteria. The results are shown in Table 2.

TABLE 2

| | | Strength of Smell |
|---|---|---|
| Present Products | Present Compound 1 | 2 |
| | Present Compound 2 | 2 |
| | Present Compound 3 | 1 |
| Comparative Products | CITRAL PGA | 5 |
| | CITRAL HGA | 5 |
| | Ethanol (blank) | 5 |

<6-level criteria>
5: Strong
4: Slightly strong
3: Moderate
2: Slightly weak
1: Weak
0: Does not smell As is evident from Table 2, it was found that the strength of isovaleric acid could be inhibited even in the experimental system by applying the present compounds exhibiting the activity of inhibiting LDH onto bare feet.

Formulation Example 1: Blended Perfume of Grape Fruit Type

| Formulation Example 1: Blended perfume of grape fruit type | |
|---|---|
| Limonene | 550 parts |
| Grape fruit oil | 100 parts |
| Geranyl nitrile | 30 parts |
| Floropal [phonetic] (= 2,4,6-trimethyl-2-phenyl-1,3-dioxane) | 30 parts |
| Tripral [phonetic] (= 2,4-dimethyl-3-cyclohexenyl carboxy aldehyde) | 10 parts |
| o-t-Butylcyclohexyl acetate | 30 parts |
| Methyl dihydrojasmonate | 50 parts |
| Total | 800 parts |

200 parts of the present compound 2 was added to 800 parts of the above blended perfume to give a blended perfume of simple grape fruit type. This perfume was used to prepare a sheet-type aromatic. This aromatic could prevent reduction in a feeling of citrus for the latter half of the usable period (3 weeks) by emission of lemon aroma.

Formulation Example 2: Blended Perfume of Fresh Muge [phonetic] type

| Formulation Example 2: Blended perfume of fresh muge [phonetic] type | |
|---|---|
| Citronellol | 300 parts |
| Phenyl ethyl alcohol | 100 parts |
| Hexyl cinnamic aldehyde | 200 parts |
| Lilial | 100 parts |
| Linalool | 50 parts |
| V-Methyl ionone | 30 parts |
| Pearide (galaxoride) | 20 parts |
| Total | 800 parts |

200 parts of the present compound 3 was added to 800 parts of the above blended perfume to give a blended perfume of floral muge type. This perfume was used to prepare a powdery detergent for clothing. Dehydrated clothes after washing with the detergent were dried and stored in a container, and after 1 or 2 weeks when the clothes were removed from the container, the clothes emitted a lemon aroma indicating that the resulting detergent has a residual aroma causing a feeling of higher cleanliness.

Formulation Example 3: Deodorant Stick

| Formulation Example 3: Deodorant stick | |
|---|---|
| The present compound 3 | 3.0% |
| Aluminum hydroxy chloride | 15.0% |
| Talc | 10.0% |
| Isopropyl myristate | 20.0% |
| Stearyl alcohol | 12.0% |
| Hardened oil | 4.0% |
| Polyoxyethylene hardened castor oil | 2.0% |
| Sesquistearate polyoxyethylene methyl glucoside | 1.0% |
| Perfume | 0.1% |
| Pure water | balance |

A deodorant stick having the above composition was prepared.

Formulation Example 4: Body Lotion

| Formulation Example 4: Body lotion | |
|---|---|
| The present compound 3 | 3.0% |
| Talc | 3.0% |
| Triethanolamine | suitable amount |
| Propylene glycol | 1.0% |
| Perfume | 0.1% |
| Ethanol | 10.0% |
| Purified water | balance |
| pH 7.2 | |

A body lotion having the above composition was prepared.

What is claimed is:

1. A citral acetal compound represented by the formula (1):

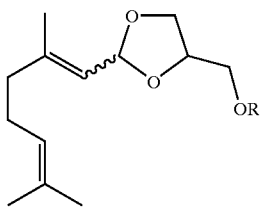

(1)

wherein the wavy line represents a cis form, trans form or a mixture thereof and R represents a $C_1$ to $C_9$ linear or branched alkyl group.

2. A perfume composition, comprising:
   the citral acetal compound according to claim 1; and
   an antioxidant.

3. A leucine dehydrogenase inhibitor, comprising:
   the citral acetal compound according to claim 1; and
   a solvent.

4. A deodorant, comprising:
   the citral acetal compound according to claim 1; and
   water.

5. A cosmetics composition, comprising:
   the citral acetal compound according to claim 1;
   wherein said composition is in the form of a stick, a cream, a milky lotion, a powder or a spray.

6. A leucine dehydrogenase inhibitor composition, comprising:
   the citral acetal compound according to claim 1; and
   a carrier.

7. A leucine dehydrogenase inhibitor composition, comprising:
   the citral acetal compound according to caim 1; and
   at least one composition selected from the group consisting of a perfume, a deodorant, a cosmetic and a skin agent for external application.

8. A method for inhibiting leucine dehydrogenase on the human skin, comprising:
   applying an effective amount of the citral acetal compound according to claim 1 onto the human skin.

9. A method of releasing an aroma of citral, comprising:
   applying an effective amount of the citral acetal compound according to claim 1 to a place where the aroma of citral is desired.

10. The perfume composition according to claim 2, wherein said antioxidant is selected from the group consisting of a phenol, a hydrochinone, tocopherol and a mixture thereof.

11. The perfume composition according to claim 2, further comprising a pH regulator.

12. The perfume composition according to claim 2, wherein said pH regulator is an organic acid, an inorganic acid or a mixture thereof.

13. The deodorant according to claim 4, wherein an amount of said citral acetal compound is 0.1 to 20% by weight.

14. The cosmetic composition according to claim 5, wherein an amount of said citral acetal compound is 0.1 to 20% by weight.

15. The cosmetic composition according to claim 5, further comprising a compound selected from the group consisting of an oil, a surfactant, an alcohol, a chelating agent, a pH adjusting agent, a preservative, a thickener, a perfume, a pigment, a UV absorber, a whitener, a wrinkle improver, a humectant, a skin-secretion inhibitor, a softener, a collagen-protecting agent, an antioxidant and a mixture thereof.

* * * * *